United States Patent
Al-Rubeai et al.

(10) Patent No.: US 7,439,037 B2
(45) Date of Patent: Oct. 21, 2008

(54) USE OF AMINOGLYCOSIDE RESISTANCE GENE

(75) Inventors: Mohamed Al-Rubeai, 3 Rachel Gardens, Birmingham (GB) B19 NY; Angelo Perani, Victoria (AU); Andy Racher, Berkshire (GB); John Birch, Oxfordshire (GB)

(73) Assignees: Mohamed Al-Rubeai, Birmingham (GB); Lonza Biologics PLC, Berkshire (GB)

(*) Notice: Subject to any disclaimer, the term of this patent is extended or adjusted under 35 U.S.C. 154(b) by 164 days.

(21) Appl. No.: 10/489,961

(22) PCT Filed: Sep. 26, 2002

(86) PCT No.: PCT/GB02/04522

§ 371 (c)(1),
(2), (4) Date: Jan. 10, 2005

(87) PCT Pub. No.: WO03/027300

PCT Pub. Date: Apr. 3, 2003

(65) Prior Publication Data

US 2005/0112722 A1    May 26, 2005

Related U.S. Application Data

(60) Provisional application No. 60/387,595, filed on Jun. 12, 2002.

(30) Foreign Application Priority Data

Sep. 26, 2001  (GB) ................. 0123098.6

(51) Int. Cl.
*C12P 21/00* (2006.01)
*C12N 5/10* (2006.01)
*C12N 15/87* (2006.01)

(52) U.S. Cl. .............. 435/69.1; 435/70.3; 435/326; 435/372.1; 435/383; 435/465

(58) Field of Classification Search ................. None
See application file for complete search history.

(56) References Cited

U.S. PATENT DOCUMENTS 5,077,214 A * 12/1991 Guarino et al. ............. 435/348
5,597,689 A *  1/1997 Devauchelle et al. ........... 435/5
5,637,477 A *  6/1997 Spaulding et al. .......... 435/69.1

FOREIGN PATENT DOCUMENTS

EP   0 481 790  * 4/1992
GB   2289946     12/1995

(Continued)

OTHER PUBLICATIONS

Sinacore, M.S., et al., 2000, "Adaptation of mammalian cells to growth in serum-free media", Molecular Biotechnology, vol. 15, pp. 249-257.*

(Continued)

*Primary Examiner*—Nashaat T. Nashed
*Assistant Examiner*—William W Moore
(74) *Attorney, Agent, or Firm*—Nixon & Vanderhye P.C.

(57) ABSTRACT

Use of aminoglycoside resistance gene product for achieving high-density growth of animal cells.

8 Claims, 6 Drawing Sheets

FOREIGN PATENT DOCUMENTS

| | | |
|---|---|---|
| WO | WO 89/01028 | 2/1989 |
| WO | WO 01/51615 A1 | 7/2001 |

OTHER PUBLICATIONS

Elias, C.B., et al., 2000, "Enhanced Growth of Sf-9 cells to a maximum density of 5.2×107 cells per mL and production of Beta-galactosidase at high cell density by fed batch culture", Biotechnology and Bioengineering, vol. 68, pp. 381-388.*

Schwartz, J.L., et al., 1997, "Production of recombinant herpes simplex virus protease in 10-L stirred vessels using a baculovirus-insect cell expression system", Journal of Industrial Microbiology & Biotechnology, vol. 19, pp. 87-91.*

Yoo, E.M., et al., 2002, "Myeloma expression systems", Journal of Immunological Methods, vol. 261, pp. 1-20.*

Hayden, M.S., et al., 1997, "Antibody engineering", Current Opinion in Immunology, vol. 9, pp. 201-212.*

Bedard, C., et al., 1994, "Maximization of recombinant protein yield in the insect cell/baculovirus system by one-time addition of nutrients to high density batch cultures", Cytotechnology, vol. 15, pp. 129-138.*

Letwin et al, A Survey of Various Media and Growth Factors Used in Cell Cultivation, 2$^{nd}$ ESACT Meeting 1978, Develop. biol. Standard. 42, 37-45.

Abstract only, GB 2 289 946 A, Cheng et al, Determining Presence of antimicrobial compounds; Dec. 1995.

Elias C.B. et al, Enhanced growth of Sf-9 cells to a maximum density of 5.2×10(7) cells per mL and production of beta-galactosidase at high cell density by fed batch culture; Biotechnol Bioeng. May 20, 2000; 68(4):381-8 (Abstract).

Krump-Konvalinkova V. et al, Fate and biological activity of exogenous DNA sequences during serial transfections in NIH/3T3 cells; Biochem Biophys Res Commun. Oct. 30, 1985; 132(2):635-44 (Abstract only).

* cited by examiner

USE OF AMINOGLYCOSIDE RESISTANCE GENE

This application is the U.S. national phase of international application PCT/GB02/04522 filed 26 Sep. 2002 which designated the U.S. and claims benefit of GB 0123098.6, dated 26 Sep. 2001 and of U.S. Provisional Application No. 60/387595 filed 12 Jun. 2002, the entire contents of each of which are hereby incorporated by reference.

The present invention relates to the field of protein expression in biotechnology. It specifically relates to the use of aminoglycoside resistance genes, in particular neomycin resistance gene, for achieving high-density growth of animal cells, a respective method of protein production and a high-density cell culture.

The biotechnological production of therapeutic proteins by means of animal cell culture is a very laborious and costly endeveaour. The efficiency of production including downstream processing is mainly governed by the space-time yield of the initial cell culture step. Both high yields and concentration of product protein in the culture broth are desired. In consequence, comparatively small increases in the maximum cell density achieved before entering the still productive stationary phase of industrial scale cell cultures, will translate in considerable enhancement of overall productivity, this being simply due to the large total number of cells added in this way.

Strongly depending on cell type and on the method of cultivation, conventional fed-batch culture systems optimized for high-density growth such as airlift reactors could not achieve growing serum-free cell cultures to a density of up to or even in excess of $10^7$ cells/ml. Higher densities are potentially achievable in serum-supplemented fed-batch culture or in the more modern perfusion reactor systems. However, both options entail serious disadvantages. Fetal bovine serum-supplemented culture media which encompass a whole range of natural growth-promoting substances are strongly dependent on the source of serum in quality and, most crucial carry the permanent risk of unintentionally introducing animal viruses into cultures producing therapeutic proteins for medical applications. Hence for regulatory reasons, serum supplementation is to be avoided.

Perfusion reactor systems however, are much more complex and demanding to control during operation and are much more costly in operation than conventional fed-batch culture systems. This is due to the permanent infusion of fresh culture medium, requiring state-of-the art microfiltration systems for parallel release of medium from the reactor. In particular jamming of the filtration unit with cellular debris or protein entails the risk of premature shut-down of operation. In comparison, fed-batch culture has significant advantages in process economics and robustness.

Further, the creation of stable recombinant cell lines producing a protein of interest requires the introduction of at least one usually constitutively expressed resistance marker gene. Expression of such marker gene constitutes an added metabolic load to the cell that may at best not impact growth behaviour or may quite adversely affect the growth rate and maximum viable cell density even in richly serum-supplemented cell culture medium (Gaigle et al., 1999, Aminoglycoside antibiotic phosphotransferases are also serine protein kinases, Chemistry and Biology 6, 11-18; Maio et al., 1991, Gene activation mediated by protein kinase C in human macrophage and teratocarcinoma cells expressing aminoglycoside phosphotransferase activity, J. Cell. Physiology 149, 548-559; Southern et al., 1982, Transformation of mammalian cells to antibiotic resistance with a bacterial gene under control of the SV40 early region promoter, J. Mol. Appl. Genet. 1, 327-341).

It is the object of the present invention to avoid the disadvantages of the prior art and to provide a method for growing animal cells to high cell density in a serum-free culture system. This object is solved by expressing aminoglycoside resistance genes in animal cells, whereafter the cells are cultured in suitable media and in a suitable culture system according to the independent claims 1, 2,8. Surprisingly, depending on the culturing method and the culture medium as is customary in the art, cell lines treated according to the present invention can grow in serum-free cell culture medium to much higher cell densities than their non-treated parent cell line. In addition, some prolongation of stationary phase growth was observed. In this way, maximum viable cell densities are achievable in serum-free culture that could not have been realized prior to the invention.

A possible embodiment of the invention is shown in the figure. What is shown is

According to the present invention, an aminoglycoside resistance gene product is used for achieving high-density growth of animal cells. The use according to the present invention comprises expressing the resistance gene product in the cells, selecting cells expressing such resistance gene product with an aminoglycoside antibiotic, preferably with the antibiotic Neomycin, which aminoglycoside is degraded by said corresponding resistance gene product, and finally cultivating such cells in a bioreactor, e.g. an airlift or stirred bioreactor, in a suitable serum-free cell culture medium allowing for such high-density growth.

A resistance gene product according to the present invention includes any aminoglycoside resistance marker such as genes known to be resistant to Gentamycin, Neomycin, Hygromycin and, in particular, to Neomycin, that can be used as a genetic marker for eukaryotic cells. Aminoglycoside resistance genes are commonly employed in the molecular biology of eukaryotic cells and are described in many standard textbooks and lab manuals (for description, ep. e.g. Shaw at al., 1993, Molecular genetics of aminoglycoside resistance genes and familial relationships of the aminoglycoside-modifying enzymes, Microbiol. Rev. 57:138-163; WO 82/03087; Southern et al., 1982, Transformation of mammalian cells to antibiotic resistance with a bacterial gene under control of the SV40early region promoter, J. Mol. Appl. Genet. 1,327-341). As can be inferred from the afore said, the aminoglycoside resistance gene product is said to be a functional gene product in view of its aminoglycoside-degrading activity according to the invention. It is therefore conceivable to employ genetically engineered, in the above sense functional variants of known aminoglycoside resistance gene products in the present invention. Such variants can be generated e.g. by substitutions, deletions, insertions or truncations of the amino acid and its encoding DNA sequence, respectively. Methods for such are well known in the art and usually comprise specific site directed mutagenesis or generation of diversity by random mutagensis of which is then followed by selecting desired variants by means of functional assays. Routine methods employed for mutagenesis may be e.g. exposure to alkylating agents or UV irradiation, error-prone PCR or related gene shuffling PCR techniques and are usually performed in microorganisms (Miller, J., Experiments in Molecular Genetics, Cold Spring Harbor Laboratory 1972; Ling et al., 1997, Approaches to DNA Mutagenesis, Analytical biochemistry 254, 157-178; Cadwell et al., 1992, Randomization of genes by PCR mutagenesis in:PCR Methods, Cold Spring Harbor Laboratory Press 1992; Moore et al., 1997, Strategies for the in vitro evolution of protein function, J. Mol. Biol. 272, 336-347).

Expediently, the resistance gene product is expressed from a DNA expression construct suited for eukaryotic expression that has been transfected into the cells by known techniques; the resistance gene product may be constitutively expressed or can be inducibly expressed or repressed, i.e. be expressable either way. At least during the periods of selection with an aminoglycoside antibiotic and during logarithmic upgrowth in a high density cell culture system for achieving maximum cell density, the resistance gene product should be expressed according to the present invention. Preferably, it is constitutively expressed e.g. from Thymidine Kinase (TK) or Siamian Virus (SV40) Late promoter, most preferably it is expressed from a strong viral enhancer-promoter constitutively active in eukaryotic cells such as e.g. Rous Sarcoma Virus (RSV)-Long Terminal Repeat (LTR)-promoter or Cytomegalovirus (CMV)-promoter. It may also be possible to employ chimeric promoters constituted of the enhancer portion of a strong viral promoter and core promoter portion of another promoter, e.g. alpha-actin promoter providing essential e.g. transcription start, TATA boxes and CAAT boxes.

An aminoglycoside according to the present invention are the commonly known aminoglycoside antibiotics (Mingeot-Leclercq, M. et al., Aminoglycosides: acitivity and resistance, 1999, Antimicrob. Agents Chemother. 43(4): 727-737) comprising at least one amino-pyranose or amino-furanose moiety linked via a glycosidic bond to the other half of the molecule. Their antibiotic effect is based on inhibition of protein synthesis. Examples are Kanamycin, Streptomycin, Gentamicin, Tobramycin, G418 (Geneticin), Neomycin B (Framycetin), Sisomicin, Amikacin, Isepamicin and the like.

In the context of the present invention, other compounds having antibiotic activity due to inhibition of protein synthesis in bacteria such as e.g. Spectinomycin, Anisomycin and in particular Puromycin, and which have chemical structures related to non-reducing amino-sugar moieties are considered being 'aminoglycoside antibiotics' according to the present invention, as is also often done in the art. It is to be noted that aminoglycoside compounds also have toxic effects in eukaryotic cell culture, partly because the mitochondrial protein translation aparatus is evolutionary of prokaryotic origin (endosymbiont hypothesis of mitochondrial evolution) though other toxicity effects are possible, too, and have been described before.

According to the present invention, for selecting cells expressing the resistance gene product, resistance selection with an aminoglycoside antibiotic is applied at least for intially selecting transfectants after transfection of the resistance gene which commonly is in the order of 48 hours up to several weeks. In consequence, the aminoglycoside resistance gene is stably transfected into the cell line. Stable transfectants commonly are genomic integrants of at least an expressed or expressable copy of the aminoglycoside resistance gene, giving rise to functional gene product. More recent approaches in genetic engineering which might devise e.g. the creation of artifical, stable minichromosomes in a cells are likewise included in the present notion of 'stable transfectant'. It goes without saying that, according to the well-known transfection protocols such as e.g. lipofection, DEAE-Dextran, Ca-phosphate or electroporation all of which are possible transfection methods according to the present invention, freshly transfected cells are first cultured in non-aminoglycoside supplemented medium before such supplement is added for selection. This intervening period of non-selection is required for efficient expression of the resistance marker gene product and is in the range of approximately 12 hours up to 1-2 days, depending on cell type. Preferably, resistance selection is applied for at least 2 weeks post-transfection, more preferably for at least 5 weeks post-transfection, most preferably for at least 8 weeks post-transfection. It is also possible to extend the period of growth under selection pressure exerted by aminoglycoside antibiotic that has been added to the medium to further cultivation of the cells, e.g. during fermentation in the bioreactor. It is also possible to apply, after the initial selection of transfectants, selection pressure in short interspersed intervals during further cultivation, by repeatedly adding single doses of aminoglycoside with the culture medium which is then replenished by non-aminoglycoside-supplemented medium. Preferably, during cultivation in a bioreactor, the expressable or expressed resistance gene according to the present invention is stably integrated into the genome and cultivation is performed in the absence of selection pressure. That is, cell culture—in e.g. a fed-batch bioreactor according to another preferred embodiment of the present invention—is carried out in the absence of an aminoglycoside antibiotic supplemented to the cell culture medium either at onset or in the course of fermentation.

Preferably, the aminoglycoside is employed in a concentration of at least 0,1 mg/ml, preferably in a concentration of at least 1 mg/ml, most preferably in a concentration of at least 4 mg/ml. Usually, such amount of aminoglycoside according to the invention is added to the cell culture medium after transfection with the expression construct for the corresponding resistance gene product, as is well-known in the art and is well-described in the standard lab manuals. In a further particularly preferred embodiment, aminoglycoside is employed in a concentration of 1 to 4 mg/ml for at least 2 weeks, more preferably for at least 5 weeks, most preferably for at least 8 weeks post-transfection during continous cell cultivation.

Preferably, the resistance gene product according to the present invention is a Neomycin-Phosphotransferase (the resistance gene usually being named Neo$^r$) as described in WO82/03087. Various natural isoforms of such phosphotransferase enzymes are known and are also comprised with the scope of the present invention. Selection with G418 (Geneticine, as defined under Chemical abstracts Registry Number 49863-47-0) or Neomycin can be used to select for cells expressing the neomycin gene product In a more preferred embodiment, G418 is used for selection of resistant cells.

The animal cells or cell line according to the present invention may be any conventional cell line used in production of recombinant protein, such as e.g. Sf9 insect cells, CHO cells, Hela cells, COS-7 cells, VERO-96 cells, HepG2 cells, BHK cells, fibroblasts, hybridoma, EBV immortalized lymphoblasts or 'myeloma' cells such as e.g. the NS0 cell line. Myeloma cells such as NS0 cells truly are B-lymphoid cell types although being routinely adressed in the art as 'myelomas' (Barnes et al., Cytotechnology 32:109-123, 2000).

Preferably, the animal cells or cell line according to the present invention are anchorage-independent cells. Such cells do not rely on substrate contact for proper growth and can grow being freely suspended in the culture medium. In a more preferred embodiment, the producer cell line are lymphoid cell lines, e.g. hybridoma cells, EBV immortalized lymphoblasts or myeloma cells, most preferably the cell line are myeloma cells and in particular myeloma NS0 cells such as e.g. cell line ECACC No. 85110503 and derivatives thereof, freely available from the European Collection of Cell Cultures (ECACC), Centre for Applied Microbiology & Research, Salisbury, Wiltshire SP4 0JG, United Kingdom. NS0 have been found to give potentially rise to extremely high product yields, in particular if used for production of recombinant antibodies. Most standard NS0 cell lines are cholesterol-dependent, making cholesterol an obligate component of the culture medium.

In a further preferred embodiment, the cell line according to the present invention that carries an aminoglycoside resistance gene is a cell line which is further capable to express recombinant glutamine synthetase (GS), more preferably it is a NS0 myeloma recombinant GS cell line. NS0 cells are specifically of advantage if used with the Glutamine synthetase (GS) expression system (Bebbington et al., 1992, High-level expression of a recombinant antibody from myeloma cells using a glutamine synthetase gene as an amplifiable selctable marker, Bio/Technology 10:169-175; Cockett et al., 1990, High level expression of tissue inhibitor of metalloproteinases in Chinese Hamster Ovary (CHO) cells using Glutamine synthetase gene amplification, Bio/Technology 8: 662-667). Preferably, the product protein gene sequence and the GS gene sequence were carried on a single GS plasmid vector for generating said transfected NS0 cell line, said genes either being expressed from different or same promoters employing e.g. internal ribosome entry sites.—The GS-system is one of only two systems that are of particular importance for the production of therapeutic proteins. In comparison to the dihydrofolate reductase (DHFR) system, the GS system, and in particular the GS system used in combination with NS0 myeloma cells, offers a large time advantage during development because highly productive cell lines can often be created from the initial pool of tranfectants thus avoiding the need for multiple rounds of selection in the presence of increasing concentrations of selective agent in order to achieve gene amplification (Brown et al., 1992, Process development for the production of recombinant antibodies using the glutamine synthetase (GS) system, Cytotechnology 9:231-236). NS0 myeloma cells are phenotypically deficient in Glutamine-synthetase. Therefore the NS0 cell line which was derived from a mouse tumour cell line (Galfre, G. and Milstein, C., Methods in Enzymol. 73, 3-75, 1981) is frequently the cell line of choice for use of the GS system at an industrial scale. An example of such a cell line is the 6A1-Neo cell line that was deposited on Aug. 30, 2002 under the treaty of Budapest under accession number 02083031 at the European Collection of Cell Cultures (ECACC), Centre for Applied Microbiology and Research, Porton Down, Salisbury/Wiltshire SP4 0JG, United Kingdom. The deposited cell line is devoid of recombinant bcl-2 and is further described in the experimental section. This cell line and any potential offspring that was engineered to produce antibody other than recombinant cB72 is a further preferred embodiment of the present invention. Such engineering may comprise cell fusion as well as silencing or knocking-out certain genes as well as more traditional techniques of creating recombinants as well as generating variants by means of mutagenesis methods (as set forth in more detail above) or traditional medium adaption techniques that preserve or improve for a given cell culture medium the growth properties of the parent cell line as deposited.

In a further preferred embodiment, the cells according to the present invention employed for high-density cell culture are devoid of recombinantly expressed bcl-2 protein, bcl-xl protein or another functional, functional to be understood as apoptosis-preventing, natural or genetically engineered variant of the apoptosis inhibiting-bcl-2 family (Petros et al., 2001, Solution structure of the antiapoptotic protein bcl-2, Proc. Natl. Acad. Science U.S.A., 98, 3012-3017) or species analogues of bcl-2 such as BHFR-1 of Eppstein Barr Virus, for instance, or other functional analogues of bcl-2 as reviewed in Petrosl et al. (ibd.). Such preferred embodiment can expediently be combined with another afore mentioned preferred embodiment, namely the absence of selection pressure as understood as presence of aminoglycoside antibiotic during fermentation. Surprisingly, co-expression of an aminoglycoside resistance marker and bcl-2 protein has been found to be refractory to the cell density promoting effect of aminoglycoside resistance according to the present invention. Without being bound by theory, the growth promoting effect of the present invention therefore does not seem to be attributable to an anti-apoptotic effect or bcl-2 based effect, since co-expression e.g. bcl-2 and Neo$^r$ should in that case be epistatic rather than being refractory to high-density growth as has actually been observed in comparative experiments.

Suitable media and culture methods for mammalian cell lines are well-known in the art, as described in U.S. Pat. No. 5,633,162 for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f 1967), L-15 medium (Leibovitz, A. et al., Amer. J. of Hygiene, 78, 1p. 173 ff, 1963), Dulbecco's modified Eagle's medium (DMEM), Eagle's minimal essential medium (MEM), Ham's F12 medium (Ham, R. et al., Proc. Natl. Acad. Sc.53, p288 ff. 1965) or Iscoves' modified DMEM lacking albumin, transferrin and lecithin (Iscoves et al., J. Exp. med. 1, p. 923 ff., 1978). It is known that such culture media can be supplemented with fetal bovine serume (FBS, also called FCS), the latter providing a natural source of a plethora of hormones and growth factors.

During transfection and selection with aminoglycosides, any medium suited for sustaining growth of the cultured animal cells can be employed. For high-density growth of the animal cells in a fed-batch bioreactor according to the present invention, a high-density growth culture medium has to be employed.

According to the present invention, a cell culture medium will be a high-density growth culture medium by definition if the culture medium allows for growth of animal cells up to or in excess of a density of viable cells of $10^6$ cells/ml in a conventional fed-batch bioreactor system. In the context of the present invention, such culture medium gives rise to even higher cell densites in combinantion with the afore described aminoglycoside selection. Usually, such a medium according to the present invention will comprise 1-10 g/l Glucose or another source of energy, the concentration of glucose being controlled at this level during fed-batch cultivation. Preferably, the medium will comprise at least 2 g/l Glucose, this concentration essentially being controlled during fed-batch fermentation. The medium is isotonic, namely being in the range of 270-320 mOsm/kg, preferably at 280-300 mOsm/kg. Individual preferences of certain cell types, e.g. lymphoid cells, for certain media are well-known in the art, and are complexly correlated with the range, proportion and individual dosing of nutrients. Examples of a high-density growth media suited e.g. for hybridoma cell lines as compared to the standard media mentioned above are given in GB2251 249 A; such high-density growth media can be usually supplemented with nutrients such as all amino acids, energy sources such as glucose in the range given above, inorganic salts, vitamins, trace elements (defined as inorganic compounds usually present at final concentrations in the micromolar range), buffers, the four nucleosides or their corresponding nucleotides, antioxidants such as Glutathione (reduced), Vitamine C and other components such as important membrane lipids, e.g. cholesterol or phosphatidylcholine or lipid precursors, e.g. choline or inositol. A high-density medium will be enriched in most or all of these compounds, and will, except for the inorganic salts based on which the osmolarity of the essentially isotonic medium is regulated, comprise them in higher amounts (fortified) than the afore mentioned standard media as can be incurred from GB2251 249 in comparison with RPMI 1640. Preferably, a high-density culture medium according to the present invention is balancedly fortified in that all amino acids except for Tryptophane are in excess of 75 mg/l culture medium. Preferably, in conjunction with the general amino acid requirement, Glutamine and/or Asparagine are jointly in excess of 1 g/l, more preferably of 2 g/l culture medium. It goes without saying that the latter preferred embodiment is less suitable in case of a recombinant cell line transfected with a Glutamine synthetase (GS) vector. In such a cell line, an excess of e.g. glutamine stemming both from exogenous and endogenous source would lead to production of ammonia which is to be avoided. Culture conditions for GS transfected cell lines are described in the examples.

Expediently, the high-density cell culture medium according to the present invention is devoid of fetal calf serun (FCS or FBS), which is being termed 'serum-free'. It has not only been devised possible, according to the present invention, to achieve high-density growth at a viable cell density of or in excess of $10^7$ cells/ml with serum-free medium, but it has surprisingly been found that supplementation with fetal serum is refractory to high-density growth of at least some cell lines tested in the context of the present invention, contrary to the usual expectations of the person skilled in the art. Cells in serum-free medium generally require insulin and transferrin in a serum-free medium for optimal growth. Transferrin may at least partially be substituted by non-peptide siderophores such as tropolone as described in WO 94/02592. Most cell lines require one or more of synthetic growth factors (comprising recombinant polypeptides), including e.g. epidermal growth factor (EGF), fibroblast growth factor (FGF), insulin like growth factors I and II (IGFI, IGFII), etc. Other classes of factors which may be necessary include: prostaglandins, transport and binding proteins (e.g. ceruloplasmin, high and low density lipoproteins, bovine serum albumin (BSA)), hormones, including steroid-hormones, and fatty acids. Polypeptide factor testing is best done in a stepwise ashion testing new polypeptide factors in the presence of those found to be growth stimulatory. There a several methodological approaches well-known in animal cell culture, an exemplary being described in the following. The initial step is to obtain conditions where the cells will survive and/or grow slowly for 3-6 days after transfer from serum-supplemented culture medium. In most cell types, this is at least in part a function of inoculum density. Once the optimal hormone/growth factor/polypeptide supplement is found, the inoculum density required for survival will decrease.

In a more preferred embodiment, the cell culture medium is free of growth factors, meaning that it is free of fetal serum or of addition of essentially pure protein growth factors that are triggering signal transduction and cell cycle progression, respectively. Such medium may still comprise other proteins such as insulin or transferrin, useful for recruiting iron from the medium, or BSA required for delivery of lipids such as cholesterol. More preferably, such medium is employed according to the present invention in conjunction with lymphoid cell lines, most preferably in conjunction with myeloma cell lines, in particular NS0 cell lines.

Suitable bioreactors according to the present invention are batch bioreactors as e.g. airlift bioreactors or stirred bioreactors as routinely employed for high-density animal cell culture. Expediently, for high-density cell culture such bioreactor will be operated in a fed-batch mode. This definition includes continous feed operation as well. Preferably, fed-batch bioreactors according to the present invention have a volumetric oxygen mass transfer coefficient $K_L a$ (as defined in Bailey, J. et al., Biochemical Engineering Fundamentals, McGraw-Hill, N.Y. 1986) of at least $6\,h^{-1}$, more preferably of at least $10\,h^{-1}$. Most preferably, a fed-batch bioreactor having said preferred oxygen mass transfer properties according to the present invention is an airlift bioreactor. Airlift bioreactors are well-known to the skilled person and the crucial parameters for reactor design have been well described (for review, see e.g. Chisti, M. et al., 1987, Airlift reactors, Chem. Eng. Commun. 60, 195-242; Koch, A. et al., 1987, Measurement and modeling of mass transport in airlift-loop reactors in relation to the reactor design, Chem. 1 ng. Tech. 59, 964-965). Though being self-evident, it is emphasized that fed-batch culture according to the present invention does not comprise perfusion culture systems.

In the context of the present invention, high-density cell culture is defined as a population of animal cells having a density of viable cells of at least or in excess of $10^6$ cells/ml, preferably of at least or in excess of $10^7$ cells/ml, more preferably in excess of $1.2\, 3\times10^7$ cells/ml, most preferably in excess of $1.3\times10^7$ cells/ml, and which population has been continously grown from a single cell or inoculum of lower viable cell density in a cell culture medium in a constant or increasing culture volume.

In a further preferred embodiment, the fed-batch culture is a culture system wherein at least Glutamin, optionally with one or several other amino acids, preferably glycine, is fed to the cell culture as described in GB2251 249 for mantaing their concentration in the medium, apart from controlling Glucose concentration by spearate feed. More preferably, the feed of Glutamin and optionally one or several other amino acids is combined with feeding one or more energy sources such as glucose to the cell culture as described in EP-229 809-A. Feed is usually initiated at 25-60 hours after start of the culture; for instance, it is useful to start feed when cells have reached a density of about $10^6$ cells/ml. The total glutamine and/or asparagine feed (for substitution of glutamine by asparagine, see Kurano, N. et al., 1990, J. Biotechnology 15, 113-128) is usually in the range from 0.5 to 3 g per 1, preferably from 1 to 2 g per 1 culture volume; other amino acids that can be present in the feed are from 10 to 300 mg total feed per litre of culture, in particular glycine, lysine, arginine, valine, isoleucine and leucine are usually fed at higher amounts of at least 150 to 200 mg as compared to the other amino acids. The feed can be added as shot-addition or as contionusly pumped feed, preferably the feed is almost contionusly pumped into the bioreactor. It goes without saying that the pH is carefully controlled during fed-batch cultivation in a bioreactor at an approximately physiological pH optimal for a given cell line by addition of base or buffer. When glucose is used as an energy source the total glucose feed is usually from 1 to 10, preferably from 3 to 6 grams per litre of the culture. Apart from inclusion of amino acids, the feed preferably comprises a low amount of choline in the range of 5 to 20 mg per litre of culture.

Preferably, the animal cell or cell line according to the present invention is a producer cell line which produces a second product protein or is capable of expressing a second product protein, e.g. upon induction. According to the present invention, the second product protein is the protein that is sought to be produced and harvested in high amount. It may be any protein of interest, e.g. therapeutic proteins such as interleukins or enzymes, e.g. enzyme inhibitors or antibodies or fragments thereof (a fab fragment for instance). It can be a recombinant protein, carried on a plasmid or another type of vector including genetically engineered viruses, or it can be stably integrated in the genome of the cell by any technique. It can also be a naturally occuring expression construct such as an antibody secreted by plasma or hybridoma cells. The product protein may include a signal sequence allowing secretion of the polypeptide from the host producer cell. It may be constitutively expressed or may be inducibly expressed.

Preferably, the product protein is a recombinant protein, most preferably a recombinant protein expressed from a constitutive promoter. 'Recombinant' according to the present invention means a protein expressed from at least one exogenous copy of the corresponding gene in a cell line that has originally been introduced into said cell line by any technique of genetic engineering, irrespective of whether the very protein is occuring in the producer cell line in at least one naturally present copy. Such additional copies of a recombinant gene can e.g. be integrated in the genome or can be carried on an episomal element. Both stable or transient expression can be employed. Any known expression vector technology, including genetically engineered viruses, can be used according to the present invention. More preferably, the recombinant protein is a chromosomally stably integrated protein.

In a further preferred embodiment of the present invention, the product protein is a secreted protein. More preferably, the product protein is an antibody or engineered antibody or a fragment thereof, most preferably it is an Immunoglobulin G (IgG) antibody.

A respective method of protein expression and further a high density cell culture corresponding with what has been said in the preceding sections on use of aminoglycoside resistance gene product are further objects of the present invention. The description of possible and preferred embodiments in the foregoing apply likewise to these objects.

EXAMPLES

1. Generation of Cell Lines and Plasmids

Figure 3:
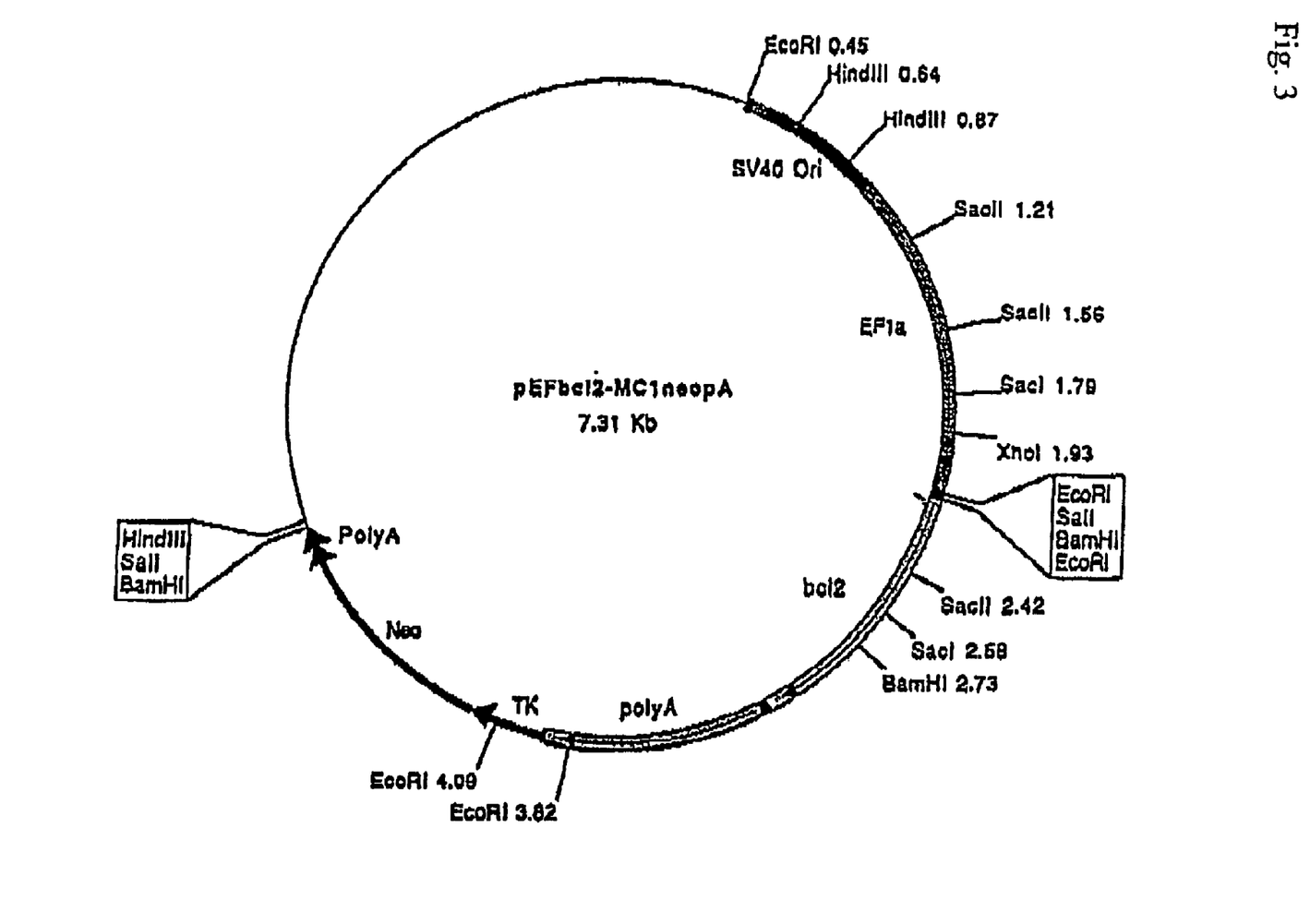
FIG. 3: Plasmid map pEF-bcl-2
Figure 4:
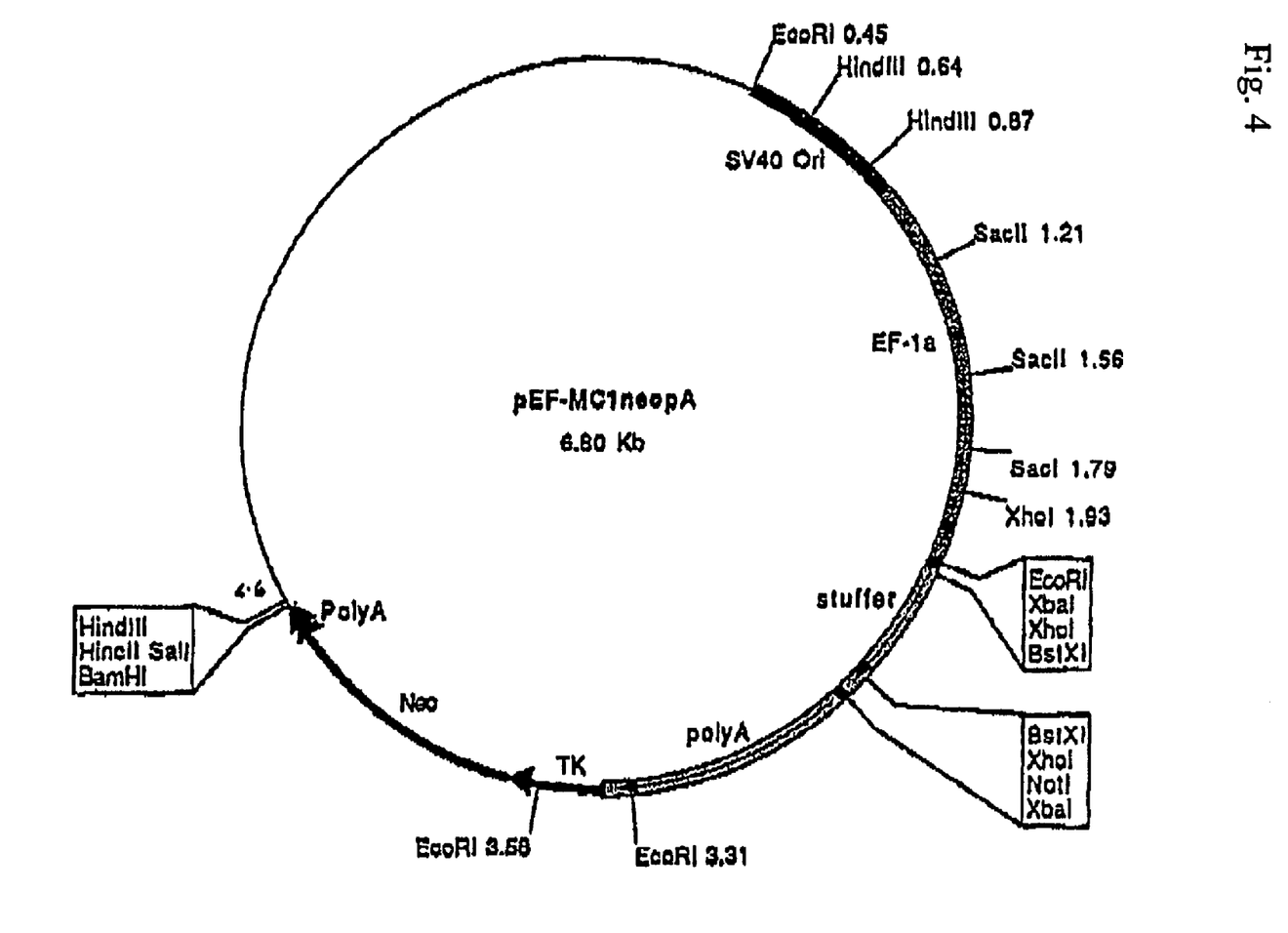
FIG. 4: Plasmid map pEF-Neo

The NS0 6A1 (100)3 cell line (6A1 for short; Lonza Biologics plc., Slough/UK) secretes a a human-mouse chimeric IgG antibody (cB72.3) from a stably integrated recombinant glutamine synthetase (GS) expression construct. Recombinant cell lines carrying Neomycin resistance were obtained by transfection of the 6A1 cell line with plasmid vectors either dicistronically expressing bcl-2 and Neo$^r$ or solely expressing Neo$^r$ from a single plasmid construct. For generation of pEF-Neo$^r$, the MC1 Neo poly A cassette from pMC1neopA (Stratagene) was inserted into pEF BOS (Mizushima et al., 1990, pEF BOS, A powerful manumalian expression vector, Nucleic Acids Research 18, 5322) which has the stuffer, to make pEF MC1 neo poly A (Visvader et el., Mol. Cell Biol. 1995 February;15(2):634-41). FIG. 4 shows the plasmid map. For generation of pEFbcl-2-Neo$^r$, the EcoRI/Taq I fragment of human bcl-2 cDNA (long anti-apoptotic transcript version, Cleary et al., Cell 47: 19-28(1986)) was subcloned into pIC194 (Gene32:482, 1984) opened with EcoRI/ClaI and excised as SalI (blunt)/EcoRV fragment that was further cloned into the blunted XbaI site of the multiple cloning site (MCS) of pEF-MClneopk bcl-2 is thus expressed from the Elongation Factor (EF) 1-a promoter (plasmid map, FIG. 3). The Neo$^r$-expression cassette (MClneopA) is an integral part of the pEF-Vector, though in the pEF-Neo vector construct finally employed, the MCS beyond the EF1-a promoter was opened at the Xho I site, blunted and a random stuffer 300 bp fragment from a non-coding sequence was inserted for proper control (plasmid map, FIG. 4). Lipofectin (Gibco, Paisely, Scotland)-mediated transfection was performed according to the manufacturers protocol. Plasmid transfectants were selected with 1 mg/ml G418 in GMEM medium (Gibco) supplemented with 5% fetal calf serum and further supplements as described in Tey et al. (Tey, B. et al., Bcl-2 mediated suppression of apoptosis in myeloma NS0 cultures, J. Biotechnology, 79(2000), 147-159). Stable transfectants were then adapted to serum-free high-density growth medium EX-CELL 302.

2. High Density Fed-Batch Cell Culture

Figure 1:
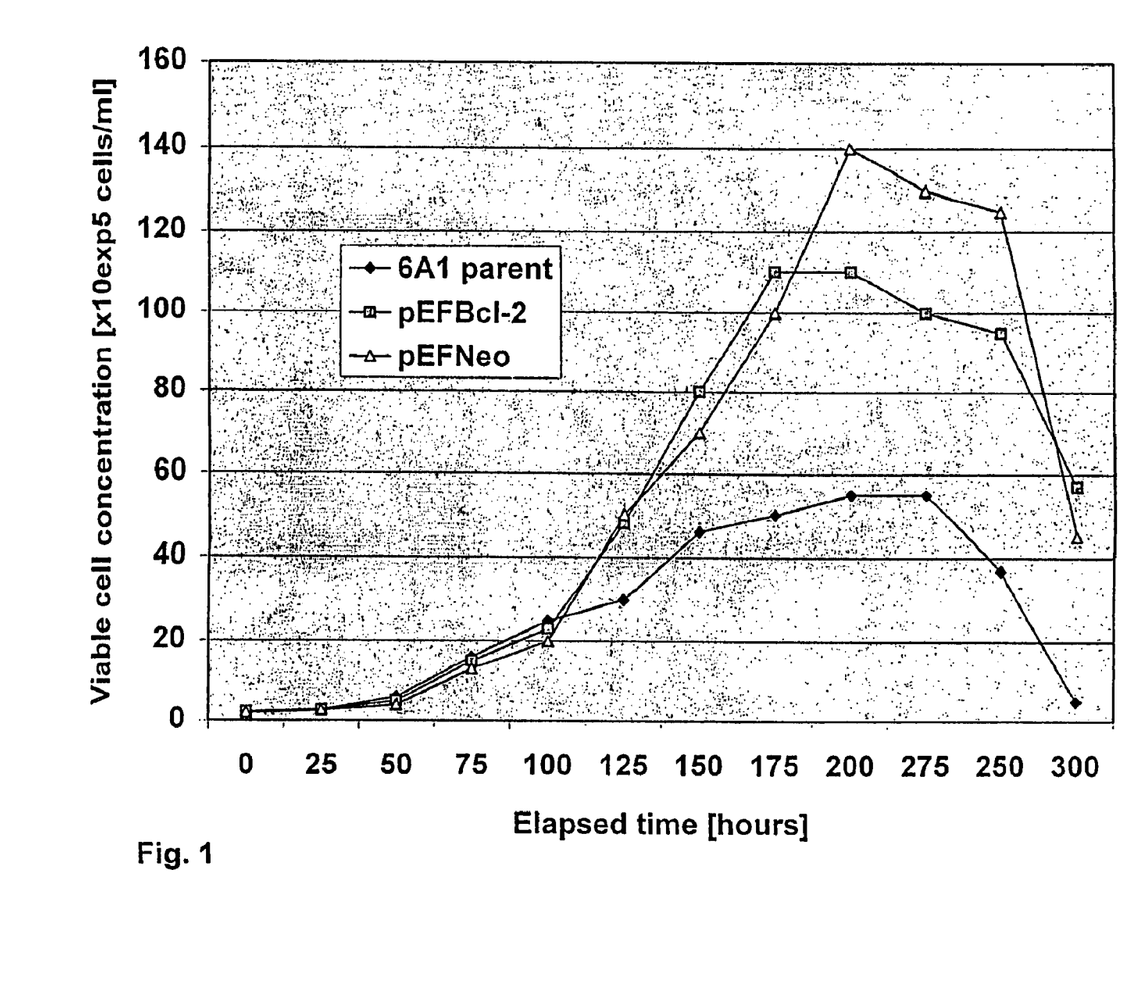
FIG. 1: Viable cell densities during growth of Neo-transformed NS0 cell line in a 10 l fed-batch airlift reactor system in comparison with a parent and a bcl-2 transformed cell lir

For high density cell culture, the NS0 6A1 parent cell line, 6A1 Neo-cell line and the 6A1 bcl-2/Neo control cell line were adapted to serum-free medium EX-CELL 302 (JRH Biosciences Inc., KS/U.S.A.) supplemented with 1 ml/50 ml GSEM (GS expression medium supplement, product number G9785, Sigma, Poole, UK). Whilst passaging, 25 µM MSX and 0.7 g/l G418 were supplemented to the medium but were omitted from inoculum and bioreactor culture medium. Density of viable cells during bioreactor cell culture is shown in FIG. 1 for culture of individual cell lines. Fed batch culture for each cell line was set up as follows:

The myeloma cell line was grown in a 10 l airlift fermenter in serum-free EX-CELL 302 medium. The starting cell population density was approximately $10^5$ cells/ml from fresh mid-exponential culture. After continous growth to a density of about $10^6$ cells/ml, shot additions of supplements were made and the pumped supplement iniated (Table 1). Feed was continous over 100 h. pH was controlled at about pH 7. Culture density was determined approx. every 25 hours by counting and cell viability was determined by Trypan blue exclusion. For total and viable cell concentration, an appropriately diluted sample was diluted with Trypan Blue (Sigma, Poole, UK) followed by a microscopic examination using a modified Fuchs-Rosental haemocytometer. For counterchecking, a CASY counter was used to measure the total and viable cell concentrations, based on cell size.

TABLE 1

| | Component | Addition [mg/L of culture] | Mode of addition |
|---|---|---|---|
| Supplement A | L-glutamine | 250-350 | shot-fed as 200 mM solution when culture is at $10^6$ cells/ml |
| Supplement B | L-cystine | 10-40 | shot-fed as 200 mM solution when culture is at $10^6$ cells/ml |
| | L-tyrosine | 40-70 | |
| | L-tryptophan | 10-20 | |
| Supplement C | L-lysine HCl | 100-140 | pump-fed as concentrated solution in PBS. Feed initiated when culture is |
| | L-histidine | 30-40 | |
| | L-arginine HCl | 60-90 | |

TABLE 1-continued

| Component | Addition [mg/L of culture] | Mode of addition |
|---|---|---|
| L-glycine | 10-30 | at $10^6$ cells/ml |
| L-valine | 60-80 | |
| L-methionine | 20-30 | |
| L-threonine | 40-60 | |
| L-serine | 20-40 | |
| L-isoleucine | 80-100 | |
| L-leucine | 70-90 | |
| L-phenylalanine | 40-60 | |
| L-glutamine | 1000-1250 | |
| D-glucose | 4000-5000 | |
| Choline chloride | 5-15 | |
| Cholesterol (+BSA) | 5-20 | |
| L-carnitine | 5-20 | |

Whereas the bcl-2/Neo recombinant cell line grew to a maximum density of viable cells of only about $10^7$ cells/ml, in contrast to Tey et al. who described having obtained maximum cell densities of <$10^6$ cells/ml in serum-supplemented fed-batch culture the Neo recombinant cell line grew to a maximum density of $1.4 \times 10^7$ cells/ml (FIG. 1). Viability of cells counted was determined by Trypan blue exclusion as described before.

Figure 2:
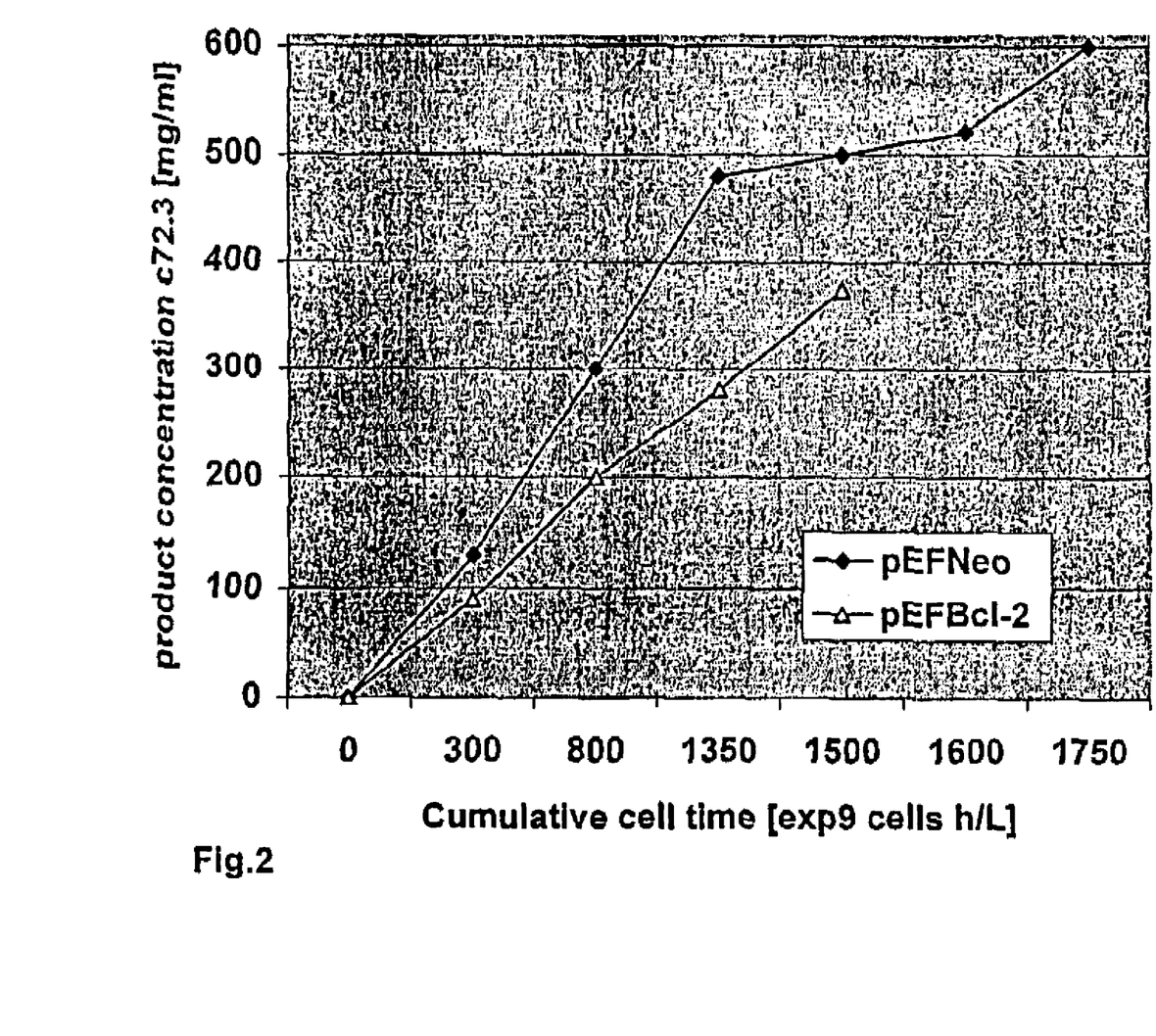
FIG. 2: Productivity for secreted antibody expressed as cumulative cell time during growth of Neo-transformed NS0 cell line in a 10 l fed-batch airlift reactor system in comparison with a bcl-2 transfected cell line.

Space time yield of recombinant antibody was in favor of the recombinant Neo cell line (FIG. 2). This is shown by graphically displaying product titer in the bioreactor versus cumulative cell time (CCT; unit: $10^9$ cell h/L). CCT was calculated by integration of the cell growth curve, essentially as described in Renard et al. (1988, Biotechnology Letters 10: 91-96). As can be inferred from FIG. 2, mean single cell productivity of the bcl-2/Neo recombinant cell line was 0.260 pg protein/cell.h, whereas the Neo cell line amounted to 0.210 pg protein/cell. The slight difference in single cell productivity ($q_p$) was clearly outnumbered at the level of total yield by the difference in viable cell densities.

3. Gene Copy Number Determination

Gene copy number of the Neomycin resistance gene was determined for the 6A1-Neo cell line as deposited by means of quantitative PCR assay, employing the 6A1 parent as a comparative standard. An gene copy number of 3.0 copies (±0.4) was determined. Given concatemeric integration of stably transfected genes, this means that single integration of the recombinant neoymcin resistance marker took place in the 6A1-Neo cell line without further amplification. This in concert with the low MSX concentrations of about 25 µM MSX; for amplification of a GS marker gene to occur 10-20× fold higher concentrations of the selection agent need to be applied. The assay was carried out by a specialized contract laboratory (Lark Technologies Inc., Houston, Tex.). Apart from testing for the neomycin resistance gene from Transposon Tn5, a negative control was establised by testing likewise for the mouse glyceraldehyde 3-phosphate dehydrogenase [GAPDH] gene. A cloned plasmid standard was used to calibrate the assay plates. Copy numbers were calculated as the number of targets (NEO) per cell (MUSGAPDH), assuming that the DNA mass of the standard diploid mammalian cell is about 6.6 pg and that GAPDH is present in two copies per cell. Genomic DNA extracted from cells was quantitated spectrophotometrically by measuimg optical densities at 260 and 280 nm as is routine in the art. For assaying neomycin resistance gene copy number, a QPCR standard curve was generated using eight dilutions of the pMC1 neopA plasmid provided by Lonza Biologics. The dilution series represented the range from $5 \times 10^6$ copies to 49 copies of plasmid DNA. Each standard was diluted into GS-NS0 control genomic DNA (equivalent to 1000 cells) in order to mimic the matrix effect of the extracted cell line DNA. Negative control reactions containing no template or containing only the control plasmid (5000 to 50 000 copies) or the DNA equivalent of 1000 GS-NS0 cells (parent cell line, about 6.6 ng) were assembled.

Copy number was determined with 95% confidence interval by determination of threshold cycle (Ct). The Ct is the fractional number at which the reporter fluorescence produced by probe cleavage crosses a fixed threshold set above the baseline. Each increase in the numerical value of Ct represents a 2× increase in target, assuming 100% PCR efficiency.

Six independent dilutions of each test article DNA were prepared and analyzed in duplicate. Each QPCR reaction contained about 6.6 ng of test sample DNA. The QPCR reactions were assembled according to the TaqMan™ Universal PCR Master Mix protocol (Applied Biosystems, Foster City, Calif.). The reactions were thermal cycled and data was collected by the ABI Prism 7700 Sequence Detection System version 1.6.3 (Applied Biosystems).

4. Comparative example

Culture of 6A1 Parent Cell Line in the Absence of Neo-Resistance Gene but in Presence of Sublethal Amounts of G418

In order to exclude any growth effect being brought forward by exposure to G418 rather than to the presence of an expressed Neomycin resistance gene, the parent cell line 6A1 was adapted to G418-containing cell culture medium. Amount of G418 could be gradually increased up to a concentration of 360 mg/ml G418 (Sigma, Poole, UK; note that lot quality of G418 may vary considerably depending on source) without abolishing cell growth. Growth medium was Lonza's optimized proprietary NS0 cell culture medium PM1 supplemented with 6 mM glutamine in the absence of fetal serum. For 6A1-Neo cell line, this serum-free medium reproducibly allowed of achieving the high cell densities of the present invention (>$2 \times 10^7$ cells/ml) as compared to bcl-2 transfectant or non-transfected parent cell line 6A1. Therefore the medium was suited to monitor potential effect of G418 adaption in the absence of neomycin marker gene.

Figure 5:
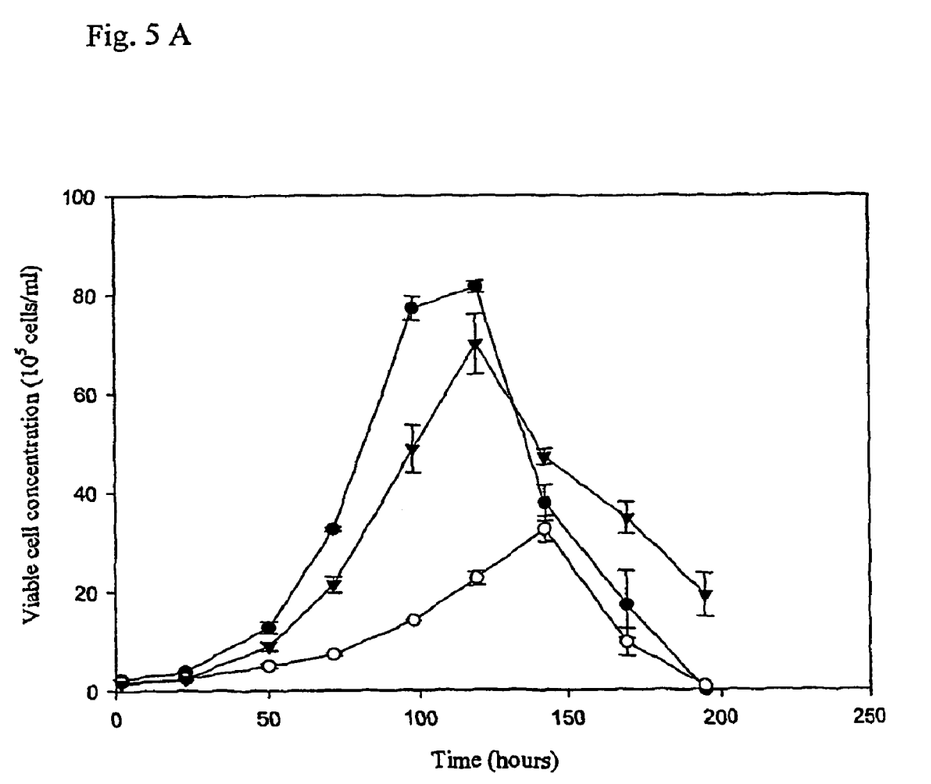
FIG. 5: Comparative growth experiment with NS0 cell line adapted to non-lethal doses of G418.

As compared to non-adapted parent cell line grown in PM1+6 mM glutamine, the adapted cells grown in G418(−) media were mildly more resistant to apoptotic and necrotic cell death (data not shown) but had lower growth rate and lower maximum cell density as compared to parent cell line (FIG. 5A: Viable cell density in batch culture of NS0 6A1 cell line/non-adapted 6A1: closed circles, 6A1 adapted to 360 mg/ml G418 grown in the presence (open circles) and absence (closed triangles) of G418). By substracting viable cell count from total cell count, the number of dead or necrotic cells was determined and is expressed in FIG. 5B as the percentage of total cell count. The experiment allowed to conclude that exposure to G418 in the absence of neomycin resistance marker therefore may account only for potential effect of apoptosis resistance but may not account for effect of enhanced high density growth behaviour. Interestingly, bioreactor culture of adapted cell line in the presence of 360 mg/l G418 even further minimized both growth rate and maximum cell density of the adapted cell line in serum-free medium PM1.

5. $q_p$ in Batch Culture of 6A1, 6A1-Neo and 6A1-bcl-2

Figure 6A:
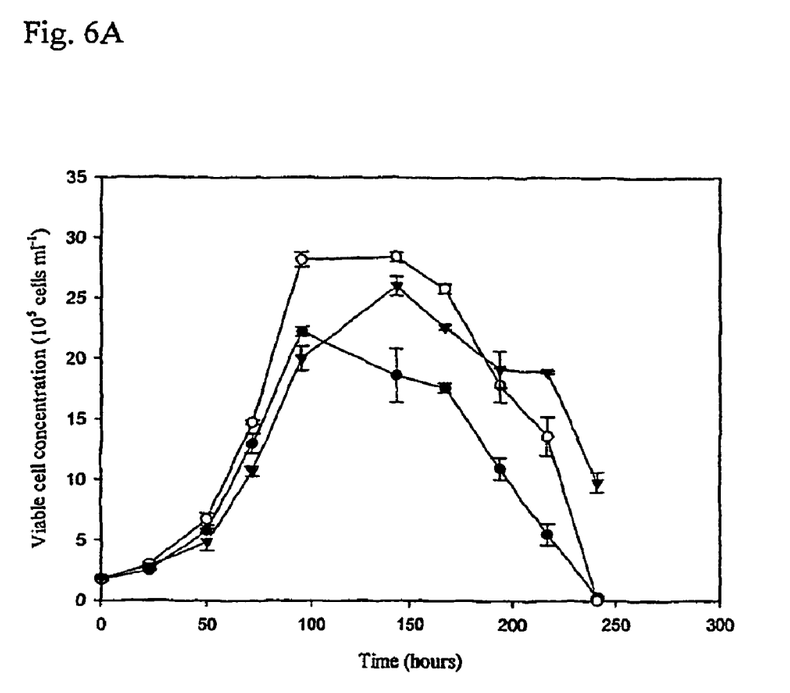
FIG. 6: Shake flask batch culture and productivity of Neo-transformed NS0 cell line in comparison with a parent and a bcl-2 transformed cell line.
Figure 6B:
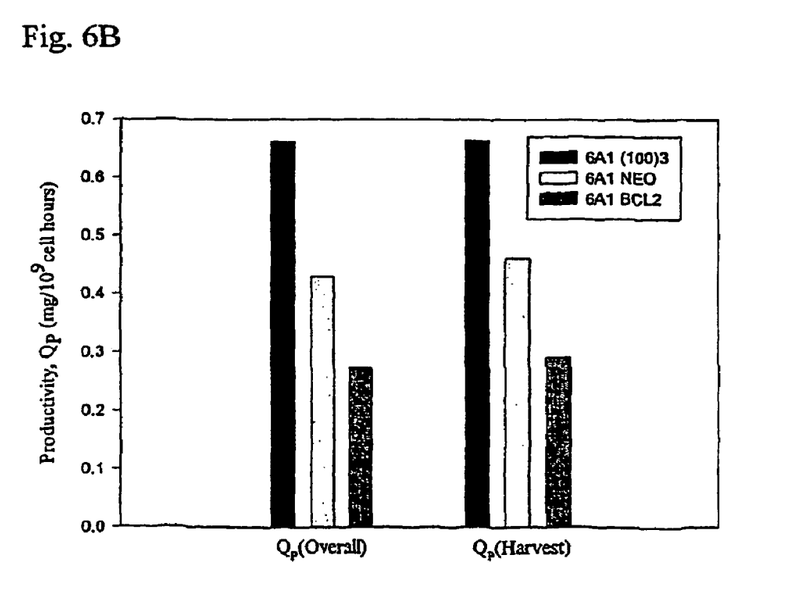

Cells lines were already described in examples 1 and 2; cell culture was carried out as described in example 2, except instead of fed-batch culture in a airlift fermenter, simple batch culture was carried out in a shake flask. Single cell productivity was determined by assaying secretion of cB72.3 in an Elisa test format from culture aliquots. Aliquots were counted for viable cell number and resuspended in fresh medium in a 96 well plate for a pre-set period of time. Culture samples were taken at about 80 hours and at harvest (about 240 hours). Results are shown in FIG. 6B. Growth curve based on viable cell density as judged by Trypan blue exclusion is shown in FIG. 6A (open circles: 6A1-Neo, closed triangles: 6A1-bcl2, closed circles: 6A1-(100)$_3$). The 6A1-Neo cell line consistingly showed higher single cell productivity qp than the 6A1-bcl-2 cell line. The parent 6A1 cell line has an ever higher $q_p$ that is negatively balanced by its much lower growth potential.

The invention claimed is:

1. A method of protein expression, comprising
   a) growing an NSO cell line to a viable cell density of at least, or in excess of, $10^7$ cells/ml in a serum-free high-density growth culture medium in a fed-batch bioreactor which NSO cell line is transfected with an aminoglycoside resistance gene and is transfected with a glutamine synthetase gene, wherein the NSO cell line expresses the aminoglycoside resistance gene product and the glutamine synthetase and further expresses a product protein, and
   b) isolating the product protein from the NSO cell culture.

2. The method of claim 1 wherein the aminoglycoside resistance gene is the neomycin resistance gene.

3. The method of claim 1 wherein the product protein is a recombinant protein.

4. The method of claim 3 wherein the recombinant protein is a secreted protein, an antibody or an antibody fragment.

5. The method of claim 4 wherein the antibody or antibody fragment is an IgG antibody or an IgG antibody fragment.

6. A high-density cell culture, comprising an NSO cell line contained in a liquid medium in a fed-batch bioreactor in a high-density growth serum-free cell culture medium, wherein the NSO cell culture has a density of viable cells in excess of $10^7$ cells per ml and wherein the NSO cell line is transfected with an aminoglycoside resistance gene and a giutamine synthetase gene and expresses the aminogiycoside resistance gene product and the giutamine synthetase.

7. The cell culture according to claim 6, wherein the aminogiycoside resistance gene is the neomycin resistance marker gene.

8. The cell culture according to claim 6, wherein the cells lack the expression of a recombinant bcl-2 or a functional variant thereof.

* * * * *